United States Patent [19]

Snoke et al.

[11] 4,374,930
[45] Feb. 22, 1983

[54] METHOD FOR THE PURIFICATION OF CHOLESTEROL OXIDASE

[75] Inventors: Roy E. Snoke, Webster; Charles T. Goodhue, Rochester, both of N.Y.

[73] Assignee: Eastman Kodak Company, Rochester, N.Y.

[21] Appl. No.: 312,474

[22] Filed: Oct. 19, 1981

[51] Int. Cl.$^3$ .............................................. C07G 7/028
[52] U.S. Cl. ..................................... 435/190; 435/815
[58] Field of Search ................................. 435/190, 815

[56] References Cited

U.S. PATENT DOCUMENTS 4,043,870  8/1977  Evans .................................. 435/190

FOREIGN PATENT DOCUMENTS 54-37885  3/1979  Japan .................................. 435/190

OTHER PUBLICATIONS

Chemical and Pharmaceutical Bulletin, Kamei et al., vol. 26, No. 9, pp. 2799–2804, (Sep. 1978).

Primary Examiner—Lionel M. Shapiro
Attorney, Agent, or Firm—James L. Lewis

[57] ABSTRACT

A method for the purification and recovery of cholesterol oxidase is disclosed. Cholesterol oxidase is purified by a method including the steps of:

(a) contacting a solution of the cholesterol oxidase to be purified with a chromatography composition comprising an unbound water-insoluble steroid which is a nonsubstrate for cholesterol oxidase so as to adsorb the cholesterol oxidase on the steroid;

(b) separating the solution from the steroid; and (c) contacting the steroid with an eluting solution containing a surfactant at a concentration between 0.001 percent and 10 percent so as to recover the adsorbed cholesterol oxidase.

In a preferred embodiment, the solution containing the cholesterol oxidase to be purified is a microorganism growth medium having cholesterol oxidase activity and, prior to the step of contacting the solution with a steroid, the solution is contacted with an ion-exchange chromatography material. In yet another embodiment, the eluting solution containing the surfactant also contains a metal salt of a concentration of at least about 0.005 molar. There is also disclosed a method for forming a packed bed of a composition comprising the unbound steroid which comprises the step of first suspending the steroid in a water-miscible organic solvent.

12 Claims, No Drawings

METHOD FOR THE PURIFICATION OF CHOLESTEROL OXIDASE

FIELD OF THE INVENTION

This invention relates to a method for purification and recovery of cholesterol oxidase. The invention is particularly useful in obtaining substantially pure cholesterol oxidase from a microorganism growth medium having cholesterol oxidase activity. In another aspect, the invention relates to a method for forming a packed bed of a steroid which is useful in the purification and recovery of cholesterol oxidase.

DESCRIPTION RELATIVE TO THE PRIOR ART

Until the present invention, the purification of cholesterol oxidase has been a very difficult problem. For example, many microorganisms which produce cholesterol oxidase produce the enzyme in a membrane-bound form. In order to separate and purify cholesterol oxidase from these microorganisms, the cholesterol oxidase must first be separated from the membrane by detergent extraction. Then, in a complex process involving solvent-salt precipitation and amphiphilic chromatography, a product of useful purity is obtained. Other microorganisms produce cholesterol oxidase extracellularly. However, the purification and recovery of this cholesterol oxidase has also been difficult.

The process of enzyme purification has been simplified in some cases through the use of specific adsorption-desorption techniques such as hydrophobic or affinity chromatography. These techniques involve enzyme-specific ligands bound, usually covalently, to a stable support. These processes usually involve costly ligands and/or extensive experimentation to find the proper chemical reactions in order to bind the ligand to a support.

One process for purifying cholesterol oxidase which uses a specific ligand bound to a support is described in Japanese Kokai 37885/1979. In this process, a "cholesterol oxidase substrate analog" is bound to a carrier such as a high-molecular-weight polysaccharide. The process of this reference requires the use of a bile acid as the cholesterol oxidase substrate analog because the acid group is needed to attach the ligand to the carrier. For example, in the preferred embodiment disclosed in this reference, the bile acid analog is first reacted with a carbodiimide. This carbodiimide is then reacted with the high-molecular-weight polysaccharide to form the support-bound ligand. This is a complex and time-consuming process.

One method which does not use a support to bind the ligand is described by Kamei et al in *Chem Pharm Bull*, 26 (9), 2799–2804 (1978), entitled "Purification of 3β-Hydroxysteroid Oxidase of *Streptomyces violascens* Origin by Affinity Chromatography on Cholesterol". This reference, as the title suggests, discloses the use of cholesterol itself as the ligand for affinity chromatography. In order to form a useful chromatography bed using cholesterol, the reference discloses that cholesterol is boiled so as to make the compound precipitable in water. While this process is capable of purifying cholesterol oxidase, it has several disadvantages. For example, the cholesterol oxidase is eluted from the chromatography material with a 10 percent solution of Triton TM X-100. For many purposes, this high level of Triton TM X-100 in a cholesterol oxidase solution, is itself a contaminant and must be removed. For example, it is difficult, if not impossible, to freeze-dry cholesterol oxidase from a solution which contains a high level of surfactant. In the subsequent steps which are needed to remove this high level of surfactant, an undesirable amount of the cholesterol oxidase activity is lost. Another disadvantage with this method is that the cholesterol oxidase to be purified catalyzes a reaction involving cholesterol, the chromatography material, thereby degrading it and producing undesirable hydrogen peroxide as a contaminant. The hydrogen peroxide is undesirable in the final product because it is a strong oxidizer and could decrease the enzyme stability. Also, cholesterol oxidase is frequently used in an assay in which the production of hydrogen peroxide is measured. Hydrogen peroxide as a contaminant in the enzyme preparation adversely affects an assay using this preparation.

There is a continuing need for a process for purifying cholesterol oxidase which does not involve the complexity of a supported ligand. It is desirable that any process for the purification of cholesterol oxidase produce a product which is not contaminated with high levels of surfactant or with hydrogen peroxide.

SUMMARY OF THE INVENTION

We have found that cholesterol oxidase is purified using a chromatography composition comprising an unbound water-insoluble steroid which is a nonsubstrate for cholesterol oxidase. If such a composition is used, it is possible to remove the adsorbed cholesterol oxidase from the chromatography composition with an eluting solution which contains a very low level of surfactant. The 3β steroids are capable of easily forming the required conjugate and are therefore preferred. However, 3β steroids, as well as compounds having a double bond in the 3 position, are also useful. We have also found that pretreatment of a cholesterol oxidase containing growth medium with an ion-exchange chromatography material further improves the yield of cholesterol oxidase. In a further improvement of our process, we have found that the levels of surfactant needed in the eluting solution are still further reduced by the incorporation into the eluting solution of a small amount of a metal salt. The process produces cholesterol oxidase in high yield with a very low level of surfactant contaminant and substantially no hydrogen peroxide.

In one aspect of the present invention, there is provided a method for purifying cholesterol oxidase comprising the steps of:

(a) contacting a solution of cholesterol oxidase to be purified with a chromatography composition comprising an unbound water-insoluble steroid which is a non-substrate for cholesterol oxidase so as to adsorb said cholesterol oxidase on said steroid;

(b) separating the solution from the steroid; and (c) contacting said steroid with an eluting solution containing a surfactant at a concentration between 0.001 percent and 10 percent so as to recover the cholesterol oxidase.

We have also discovered a method which is particularly suitable for forming a packed bed of the steroid which is used as the chromatography composition. Thus, in another aspect of the present invention, there is provided a method of forming a packed bed of a composition comprising an unbound water-insoluble steroid comprising the steps of:

(a) suspending the steroid in a water-miscible organic solvent;

(b) adding water to the suspension so that the final water content is between about 20 percent and 90 percent on a volume basis; and (c) pouring the suspension formed in step (b) onto filter means so as to form the packed bed.

This process produces a packed bed which is very uniform and therefore particularly useful in the process for purifying cholesterol oxidase.

DETAILED DESCRIPTION OF THE INVENTION

A steroid is a compound composed of a series of four carbon rings joined together to form a structural unit called cyclopentanoperhydrophenanthrene. The steroids which are useful in the present process are water-insoluble; that is, the steroid nucleus is not substituted with a solubilizing group such as an acid group. (By "insoluble" is meant a solubility on the same order of magnitude as cholesterol itself. Cholesterol has a solubility of less than 0.2 mg/100 mL.) For example, the bile acids which are steroids having a carboxy group are not useful in the process of the present invention because any chromatography composition comprising an unbound bile acid dissolves during the process. The preferred steroids which are useful in the present process are $3\beta$ steroids. As used throughout this specification, the numbering of the steroid nucleus, as well as the designation of the configuration of the various substituents, i.e., whether alpha or beta, follows conventional practice. The $3\beta$ steroids are capable of easily forming a cholesterol oxidase-ligand conjugate, probably because cholesterol itself has a $3\beta$ configuration, and are therefore particularly useful as chromatography compositions within the scope of the present invention. Mixtures of steroids are also useful.

Illustrative classes of compounds which are useful water-insoluble $3\beta$ steroids include cholesterol esters and ethers. These are cholesterol derivatives wherein the $3\beta$ hydroxy group of cholesterol has been converted to an ester, i.e., an OOCR group, or an ether, i.e., an OR group. For the purposes of the present process, the R group is preferably an alkyl chain of from 1 to about 18 carbon atoms. Of these, the lower alkyl groups, i.e., carbon 1-6, are preferred because they are easily dispersed in the water-miscible organic solvent which is used to form the chromatography bed and because they provide improved recovery of cholesterol oxidase in the process. Other useful R groups include aryl, such as phenyl substituted with nonsolubilizing groups, and alkyl, variously substituted with nonsolubilizing groups.

Another preferred class of water-insoluble $3\beta$ steroid compounds includes cholesterol derivatives wherein the $3\beta$ hydroxy group has been replaced with a halogen such as bromide or chloride or other ion such as nitrate, chloroformate or mercaptan.

While the cholesterol derivatives described above are the preferred water-insoluble $3\beta$ steroids, other steroids and their derivatives are also useful. Other useful steroids include $\beta$-estemloil and plant sterols such as sitosterol, stigmasterol, campesterol, desmosterol and ergosterol. Certain 4-ene-3-one steroids derived from $3\beta$-sterols also are useful, for example, cholestenone and sitostenone.

Specific illustrative water-insoluble $3\beta$ steroids which are useful as the chromatography composition in the present process are as follows:

cholesteryl acetate
cholesteryl bromide
cholesteryl chloride
cholesteryl formate
cholesteryl linoleate
cholesteryl nitrate
cholesteryl oleate
cholesteryl palmitate
cholesteryl butyl ether
cholesteryl butyl ethyl ether
cholesteryl methyl ether
choles-4-ene-3-one
coprostan-3$\alpha$-ol Of the above steroids, the coprostan-3$\alpha$-ol is an example of a 3$\alpha$ steroid which is useful. Choles-4-ene-3-one is an example of a steroid having a double bond in the 3 position which is useful.

The chromatography composition comprising the steroids described above is advantageously used in the form of a packed bed. By "unbound" is meant that the steroid is not reacted with a support such as the polysaccharide support of the Japanese Kokai No. 37885/1979. The composition optionally contains other components such as buffers, impurities and filter aids. In addition, the compositions optionally contain components such as polymeric beads to provide porosity to the composition. A solution of the cholesterol oxidase to be purified is simply passed over the packed bed of the described steroid. The cholesterol oxidase is adsorbed to the steroid while the remainder of the solution passes through the packed bed and is therefore separated from the chromatography composition. The chromatography composition containing the adsorbed cholesterol oxidase is then washed with an elutant so as to remove the cholesterol oxidase. It is often desirable to wash the bed containing the adsorbed cholesterol oxidase with a buffer prior to washing it with the elutant.

One particularly preferred method of forming the packed bed which is useful in the present process is to first suspend the described steroid (or steroid mixture) in a water-miscible organic solvent. The solvent is chosen so that it wets the surface of the steroid and allows the formation of a uniform suspension. To this suspension is added water up to about 90 volume percent. A uniform packed bed is formed by simply pouring the resulting suspension onto filter means. The filter means is a piece of filter paper or, in preferred embodiments, is in the form of a glass wool plug packed into one end of a glass tube. The result is a highly uniform packed bed in the form of a column. The packed column is washed with a large volume of water so as to remove traces of the water-miscible organic solvent. Examples of useful water-miscible organic solvents include methanol, ethanol, propanol and dimethyl sulfoxide.

The present process is useful to separate and purify cholesterol oxidase from any solution. It is particularly useful in separating and purifying cholesterol oxidase from a microorganism growth medium in which the cholesterol oxidase has been produced, e.g., a spent or at least partially spent medium. It is particularly useful in extracting cholesterol oxidase from a growth medium wherein the cholesterol oxidase has been produced extracellularly. Useful microorganisms which produce extracellular cholesterol oxidase include *Brevibacterium*

*sterolicum, Corynebacterium cholesterolicum* and *Streptomyces violascens*. Methods for producing cholesterol oxidase using these microorganisms are known in the art.

After the cholesterol oxidase has been produced by growing the microorganism aerobically, the microorganism cells are preferably filtered from the spent growth medium. If the microorganism produces the cholesterol oxidase internally, it is necessary to break open the cells, as is conventional in enzyme manufacture, prior to this filtration step. The resulting cell-free growth medium contains, in addition to the cholesterol oxidase, what remains of the initial growth medium, as well as other products of microorganism growth. While this cell-free growth medium itself is purified by contact with the water-insoluble steroid chromatography composition, in many instances it is desirable to first remove some of the other products produced by the microorganism prior to cholesterol oxidase purification. Preferably, in this pretreatment the enzyme solution is subjected to ion-exchange chromatography with the aid of DEAE or TEAE-cellulose (slightly basic anion exchanger with a diethylaminoethyl or triethylaminoethyl group on a functional group of a 3-dimensionally crosslinked polysaccharide) or CM cellulose (slightly acid cation exchanger with a carboxymethyl-functional group on a 3-dimensionally crosslinked polymer). Other useful materials for this pretreatment step are described in U.S. Pat. No. 4,055,469 to Snoke and Klein. It has been found that this pretreatment step does not result in a loss of cholesterol oxidase activity in the final product.

The solution containing the cholesterol oxidase to be purified is contacted with a water-insoluble steroid to perform the process of the present invention. This contacting step is carried out in a variety of methods such as by simply adding the steroid to a solution containing the cholesterol oxidase (batch mode) or, more preferably, through the use of a packed bed or a column prepared in the manner described above. The solution containing the cholesterol oxidase is merely poured onto the column and the cholesterol oxidase is adsorbed to the steroid. The solution minus the cholesterol oxidase is separated from the steroid by allowing the solution to pass through the column or in the batch mode by filtration.

After the cholesterol oxidase has been adsorbed to the steroid and the remainder of the solution separated, the cholesterol oxidase is released from the steroid by washing the steroid with a surfactant solution. Prior to this eluting step, the steroid with adsorbed cholesterol oxidase is optionally equilibrated to a neutral pH by washing the steroid with a buffer solution. Suitable buffers include phosphate and dimethyl glutarate.

The eluting solution is an aqueous solution containing the surfactant. Any of a wide variety of surfactants is useful including cationic and anionic surfactants, as well as nonionic surfactants. Illustrative useful surfactants include nonionic surfactants such as poly(ethylene glycols), poly(vinyl alcohols), polyethers, polyesters, polyhalides, poly(oxyethylene) alcohols, poly(glycidols), octylphenyl polyethoxy ethanols and alkyl polyethoxy ethanols. Cationic surfactants, for example, quaternary ammonium compounds such as cetyltrimethyl ammonium chloride are useful. Anionic surfactants such as deoxycholate and sodium dodecyl sulfate are also useful. The preferred surfactants are the nonionic surfactants Triton X-100 ™ (an octylphenyl polyethoxy ethanol available from Rohm and Haas Co of Philadelphia, Pa.) and Tergitol 15-S-7 ™ (an alkyl polyethoxy ethanol wherein the alkyl group has 7 carbon atoms, and available from Union Carbide). These surfactants elute a large percentage of the adsorbed cholesterol oxidase at low concentrations. Mixtures of surfactants are also useful in the eluting solution.

The amount of surfactant in the eluting solution depends primarily on the presence or absence of metal salt in the elutant. The amount of surfactant also depends, to a lesser degree, on the particular steroid, the particular surfactant and the pH, as well as other factors. The optimum amount of surfactant is easily determined once these other factors have been selected. Generally, a useful amount of surfactant in the elutant solution is between about 0.001 and about 10 weight percent. Where a metal salt is used, an elutant with a surfactant concentration on the lower end of this range is useful, while a surfactant concentration on the higher end of this range is needed when no metal salt is used. An advantage of the present invention is that, even in the absence of the metal salts, only relatively low levels of surfactant are needed. In preferred embodiments, the elutant contains 1 percent or less by weight surfactant.

In particularly preferred embodiments of the present invention, a metal salt is used in combination with a surfactant in the eluting solution. The use of a metal salt allows for removal of the cholesterol oxidase from the steroid using lesser amounts of surfactant. This is particularly surprising because a metal salt solution alone will not elute the cholesterol oxidase from the steroid and similarly very low levels of surfactants alone will not elute the cholesterol oxidase from the steroid. However, a low level of surfactant in combination with a metal salt very effectively elutes cholesterol oxidase.

Useful metal salts include the halides such as lithium, sodium or potassium chlorides or bromides. Other useful metal salts include sulfates and nitrates.

The metal salt is present in the eluting solution over a wide range of concentrations. As with the amount of surfactant, the optimum concentration of metal salt is easily determined by simple experiment once the other process parameters have been selected. Generally, the amount of metal salt is between about 0.005 and about 1.0 molar.

The elutant containing the cholesterol oxidase is useful in a variety of processes. For example, the elutant is useful directly in a wet assay for the analysis of cholesterol. Optionally, the elutant is further processed to recover the cholesterol oxidase in a dried form such as by freeze-drying.

In the examples, unless otherwise indicated, the following procedures apply:

Production of Enzyme—A species of Streptomyces, isolated from local soil, was grown aerobically in 2.8-L Fernbach flasks containing a nutrient medium. The nutrient medium contained, in 500 mL: 0.5% glycerol, 2.0% yeast extract, 0.2% phosphate plus trace salts (percentages by weight). After 24 hr, cells were removed by filtration. Cholesterol oxidase remained in the cell-free growth medium (CFM).

Sample Preparation—The cell-free filtrate (CFM), obtained from the fermentation of the Streptomyces microorganism, was a clear, dark brown fluid, pH 8.3. The dark color, caused by a pigmented material produced by the microorganism, was removed without loss of oxidase activity by adding 0.6 g DEAE cellulose per mL CFM, stirring for 20 min and filtering. The cholesterol oxidase remained in the clear, yellow-amber filtrate fraction (DE), pH 8.3. Enzyme activity was stable for at least 1 wk when stored at 4° C.

Cholesterol Oxidase Activity Assay—The enzyme activity was measured continuously by a peroxidase-coupled reaction at 37° C. and 430 nm in a Beckman 25 K spectrophotometer. The assay mixture contained in 1 mL: 50 μmoles potassium phosphate buffer, pH 7.0, 0.78 μmole cholesterol, 1% Triton TM X-100, 28 μg horseradish peroxidase (3.8 purpurogallin units) and 0.26 μmole o-dianisidine. Cholesterol was added as a 7.8 mM solution in 10% Triton TM X-100. After 5 min temperature equilibration, cholesterol oxidase was added to initiate reaction. By definition, 1 unit of cholesterol oxidase produces 1 μmole hydrogen peroxide per min at these described assay conditions.

Protein Assay—The protein assay was performed according to the Lowry procedure. Bovine serum albumin was the protein reference. (O. H. Lowry, N. T. Rosebrough, A. L. Farr and R. J. Randall, *J Biol Chem*, 193, 265-275, 1951.)

Triton TM X-100—Concentrations used in elution of the enzyme from the column bed were measured as described by Garewal (H. S. Garewal, *Anal Biochem*, 54, 319-324, 1973.)

Column Preparation and Use—Compounds to be used as column materials (adsorbents) were suspended in methanol. Water was added with stirring to about 20% final volume. Generally, the materials, wettable but insoluble in water, settled to the bottom. The suspension was poured into columns containing a glass wool plug, and a large volume of water was run through to remove traces of the solvent (methanol). The packed columns were equilibrated with 0.01 M potassium phosphate buffer, pH 7.0. Samples were applied to the packed columns, then exposed sequentially to a buffer wash and an elutant wash (either surfactant alone or surfactant plus a salt) followed by water to regenerate the adsorbent. (Adsorbent regeneration was complete when the UV-absorbance peak for Triton TM X-100 was no longer evident in the water effluent.)

In the Examples, it will be noted that in many cases more activity is recovered from the column than was originally measured in the solution to be purified. This is believed to be due, at least in part, to the removal of cholesterol oxidase inhibitors during purification.

Example 1: Purification of cholesterol oxidase

A fraction of crude enzyme in 485 mL of a cell-free medium was obtained and subjected to DEAE cellulose ion-exchange chromatography. A chromatography column was prepared using 1.0 g cholesteryl chloride and the crude enzyme (DE filtrate) was applied. The column was then washed with a buffer solution (510 mL). The adsorbed enzyme was then eluted from the column using 19 mL of 0.1% Triton TM X-100. The surfactant was subsequently removed from the preparation by adsorption onto Amberlite TM XAD-2 beads: 5 mg beads per 1 mL of 0.1% Triton TM X-100 eluate were stirred for 20 min at room temperature and then removed by filtration to produce the XAD filtrate.

Table 1 shows the analysis for each of the solutions throughout the process. The analysis was performed on an aliquot of the volume of solution used.

The specific activity of the oxidase was increased by 118-fold as a result of this process (14.2 U per mg protein vs. 0.12 U per mg protein). Also, as shown in Table 1, 68% of the starting activity (46 total units) was recovered in the final material. Prior to the XAD-2 bead filtration step, 95% (65 total units) of the starting activity was recovered.

TABLE 1

| Step | Volume mL | Protein mg/mL | Activity U/mL | Total Units | Specific Activity U/mg protein |
|---|---|---|---|---|---|
| Cell-free medium (CFM) | 485 | 1.16 | 0.14 | 68 | 0.12 |
| DEAE filtrate (DE) | 485 | 0.86 | 0.15 | 73 | 0.17 |
| cholesteryl chloride wash | 510 | ND* | 0.06 | 30 | ND |
| 0.1% Triton TM X-100 | 19 | ND | 3.42 | 65 | ND |
| XAD filtrate | 19 | 0.17 | 2.42 | 46 | 14.2 |

*ND is not determined.

Example 2: Compounds useful as adsorbents for cholesterol oxidase

Pasteur pipet columns containing 0.1 g of the test compound (shown in Table 2) were prepared as described. An enzyme preparation containing 0.45 unit of cholesterol oxidase was applied to each column. The columns were washed with 3 mL volumes of 10 mM potassium phosphate buffer, pH 7.0, and then the adsorbents were eluted from the column using 0.1% Triton TM X-100 in buffer. Generally, the surfactant eluates were clear and colorless. As shown in Table 2, cholesteryl nitrate, cholesteryl chloride and cholesteryl formate were the most effective materials used.

TABLE 2

| Compound | % of the Activity of the Original Solution Eluted |
|---|---|
| cholesteryl acetate | 78 |
| cholesteryl bromide | 78 |
| cholesteryl chloride | 116 |
| cholesteryl formate | 109 |
| cholesteryl linoleate | 29 |
| cholesteryl nitrate | 124 |
| cholesteryl oleate | 20 |
| cholesteryl palmitate | 67 |
| cholesteryl butyl ether | 78 |
| cholesteryl ethyl ether | 60 |
| cholesteryl methyl ether | 62 |
| choles-4-ene-3-one | 89 |
| coprostan-3α-ol | 89 |

Example 3: Various surfactants as elutants for cholesterol oxidase

Various surfactants, shown in Table 3, were tested as elutants for cholesterol oxidase. Pasteur pipet columns containing cholesteryl acetate (0.5 mL bed volume) were prepared, and cholesterol oxidase preparations containing 2.4 units in 2 mL were applied. Each column was eluted sequentially with 2 mL volumes of water, 0.1% surfactant and 1.0% surfactant. No activity eluted with water. As shown in Table 3, the nonionic surfactants, Tergitol TM 15-S-7, and Triton TM X-100, were most effective at 0.1% concentrations and no additional enzyme was eluted with the higher concentrations. With the deoxycholate surfactant, only 4% of the initial activity applied to the column was recovered with low levels of surfactant.

TABLE 3

| | Surfactant | % Concentration of Surfactant | Activity Recovered % of the Starting Activity |
|---|---|---|---|
| Nonionic: | Triton TM X-100 | 0.1 | 86 |
| | | 1.0 | 0 |
| | Tergitol TM 15-S-7 | 0.1 | 72 |
| | | 1.0 | 0 |
| | Zonyl TM FSN | 0.1 | 23 |
| | | 1.0 | 15 |
| Cationic: | Cetyltrimethyl-ammonium chloride | 0.1 | 58 |
| | | 1.0 | 0 |
| Anionic: | Desoxycholate | 0.1 | 4 |
| | | 1.0 | 12 |
| | Sodium dodecyl sulfate | 0.1 | 30 |
| | | 1.0 | 0 |

Example 4: Beneficial effect of salts on surfactant elution of cholesterol oxidase Pasteur pipet columns containing cholesteryl acetate (0.4 mL bed volume) were prepared, washed with 0.1% Triton TM X-100 and then with water. (Surfactant concentrations are on a weight basis.) DEAE cellulose fractions containing 1.86 units cholesterol oxidase in 2 mL were obtained as described above and applied to each column. The columns were eluted sequentially with 2 mL volumes of water, 0.005% Triton TM X-100, 0.005% Triton TM X-100 containing a salt (LiCl, NaCl or KCl) in concentrations shown in Table 4. It was observed that 0.005% concentrations of Triton TM X-100 alone did not elute cholesterol oxidase from the columns. Also, salts alone in gradients from 0.01 to 1.0 M were found to be ineffective as elutants. However, when small amounts of Triton TM X-100 (0.005%) were combined with salts from 0.01 to 0.5 M concentrations as shown in Table 4, enzyme recovery was excellent, especially with 0.01 M and 0.05 M LiCl. After the columns were eluted with the 0.005% Triton TM X-100-salt solutions, they were eluted with a 0.1% Triton TM X-100 solution. In each case substantially all of the remainder of the initial cholesterol oxidase activity was removed from the column.

TABLE 4

| | Salt Concentration (M) | | | | | | |
|---|---|---|---|---|---|---|---|
| Elutant | 0 | 0.01 | 0.025 | 0.05 | 0.10 | 0.25 | 0.5 |
| | Activity Released (% of the Starting Activity) | | | | | | |
| LiCl + 0.005% Triton TM | 0 | 71 | 47 | 75 | 54 | 62 | 62 |
| NaCl + 0.005% Triton TM | 0 | 31 | 39 | 43 | 39 | 26 | 60 |
| KCl + 0.005% Triton TM | 0 | 39 | 50 | 61 | 27 | 24 | 29 |

Example 5: Effect of extraneous materials on purification process

Two fractions, one obtained directly from the cell-free medium (CFM) and the second further subjected to DEAE cellulose chromatography (DE), were applied to separate columns containing 1.0 g each of cholesteryl chloride. The columns were eluted with 10 mM phosphate buffer, then with 0.1% Triton TM X-100 and the activities of the resulting enzyme preparations were assayed. The activity adsorbed from the CFM fraction was 9.2 U compared with 19.2 U from the DE fraction.

Example 6: Repeated use of cholesteryl acetate and cholesteryl chloride columns to adsorb cholesterol oxidase Columns containing 0.1 g of cholesteryl acetate and 0.1 g of cholesteryl chloride were prepared. Various concentrations of cholesterol oxidase (shown in Table 5) were applied to each column. Each column was washed with 3 mL of 10 mM potassium phosphate buffer, pH 7.0, and then the enzyme was eluted using 3 mL of 0.1% Triton TM X-100 in that buffer. Water was run through the columns to remove residual Triton TM X-100 and to regenerate the adsorbents. Cholesterol oxidase was applied to these columns again, and the procedure was repeated for a total of 6 times. As shown in Table 5, each adsorbent was regenerated by the water wash between runs.

TABLE 5

| | | Units Eluted from | |
|---|---|---|---|
| Run | Units Applied | Cholesteryl Acetate | Cholesteryl Chloride |
| 1 | 0.45 | 0.35 | 0.52 |
| 2 | 0.32 | 0.37 | 0.43 |
| 3 | 0.44 | 0.50 | 0.53 |
| 4 | 0.44 | 0.53 | 0.56 |
| 5 | 0.43 | 0.49 | 0.52 |
| 6 | 0.41 | 0.47 | 0.49 |

Although the invention has been described in considerable detail with particular reference to certain preferred embodiments thereof, variations and modifications can be effected within the spirit and scope of the invention.

We claim:

1. A method for purifying cholesterol oxidase comprising the steps of:
   (a) contacting a solution of the cholesterol oxidase to be purified with a composition comprising an unbound water-insoluble steroid which is a nonsubstrate for cholesterol oxidase so as to adsorb said cholesterol oxidase on said steroid;
   (b) separating said solution from said steroid; and
   (c) contacting said steroid with an eluting solution containing a surfactant at a concentration between 0.001 percent and 10 percent by weight so as to recover said cholesterol oxidase.

2. A method for recovering cholesterol oxidase from a microorganism growth medium in which said cholesterol oxidase has been produced, said method comprising the steps of:
   (a) adding an ion-exchange chromatography material to said medium;
   (b) filtering said medium;
   (c) contacting the filtrate from step (b) with a composition comprising an unbound water-insoluble steroid which is a nonsubstrate for cholesterol oxidase so as to adsorb said cholesterol oxidase on said steroid;
   (d) separating said filtrate from said steroid; and
   (e) contacting said steroid with an eluting solution containing a surfactant at a concentration between 0.001 percent and 10 percent by weight so as to recover said cholesterol oxidase.

3. A method according to claims 1 or 2 wherein said steroid is a 3β steroid.

4. A method according to claims 1 or 2 wherein said eluting solution contains 1 percent or less surfactant by weight.

5. A method according to claims 1 or 2 wherein said unbound steroid is in the form of a packed bed.

6. A method according to claims 1 or 2 wherein said eluting solution contains a metal salt at a concentration of at least about 0.005 molar.

7. A method according to claims 1 or 2 wherein said eluting solution contains a metal salt at a concentration of at least about 0.005 molar, wherein the metal of said salt is selected from the group consisting of lithium, sodium and potassium.

8. A method according to claims 1 or 2 wherein said steroid is a 3β ester or ether of cholesterol wherein the ester or ether radical contains from 1 to 6 carbon atoms.

9. A method according to claims 1 or 2 wherein said steroid is cholesterol substituted in the 3β position with a group selected from a halogen, nitrate and formate.

10. A method according to claims 1 or 2 wherein said steroid is selected from the group consisting of cholesteryl nitrate, cholesteryl chloride and cholesteryl formate.

11. A method according to claims 1 or 2 wherein the surfactant in said eluting solution is a nonionic surfactant.

12. A method according to claims 1 or 2 wherein said surfactant is selected from the group consisting of octylphenyl polyethoxy ethanols and alkyl polyethoxy ethanols.

* * * * *